Dec. 3, 1957 P. DOT Plant Pat. 1,663
ROSE PLANT
Filed April 4, 1957
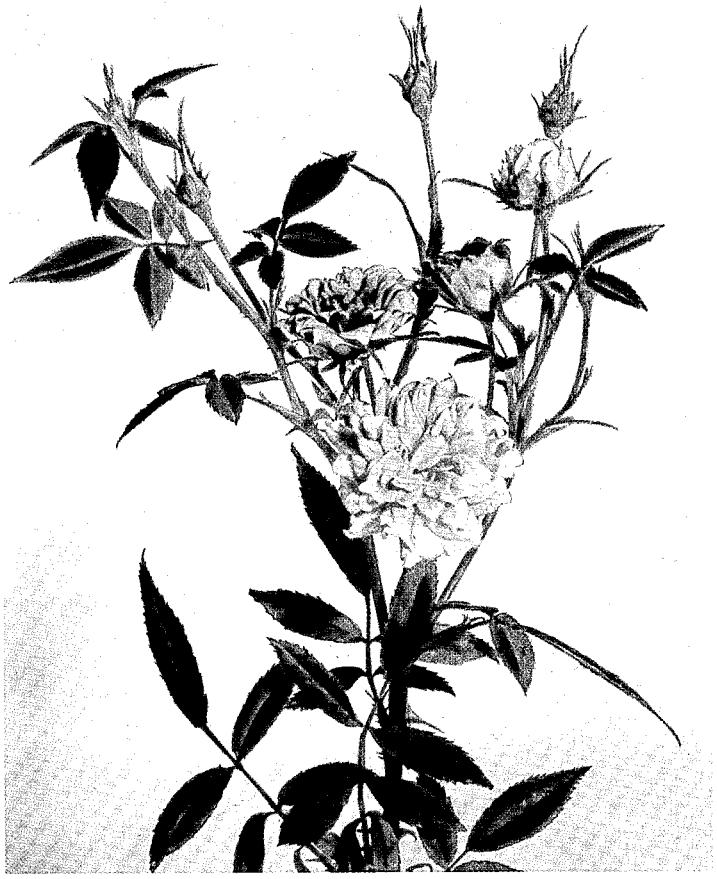
Inventor.
Pedro Dot
By: Robb & Robb
Attorneys United States Patent Office Plant Pat. 1,663
Patented Dec. 3, 1957

1,663

ROSE PLANT

Pedro Dot, Barcelona, Spain, assignor to The Conard-Pyle Company, West Grove, Pa., a corporation of Pennsylvania Application April 4, 1957, Serial No. 650,806

1 Claim. (Cl. 47—61)

The present invention relates to a new and distinct variety of rose plant of the miniature rose class, which was originated by me by crossing the variety "Perla de Montserrat" (unpatented) with the variety "Perla de Alcanada" (unpatented).

As a result of this breeding, I have produced a new variety which is distinguished from its parents by the following dominant characteristics which are not found in combination in any other variety of miniature rose presently known in commerce:

(1) The small, compact, yet vigorous habit of growth;

(2) The clean and attractive foliage of appropriate size;

(3) The outstandingly good fluorifernousness of the plant;

(4) The very double blooms of very good forms; and (5) The Tyrian Purple general color tonality of the blooms.

Asexual reproduction of my new variety by budding and by own root cuttings, as performed at West Grove, Pennsylvania, U. S. A., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the Royal Horticultural Society, except where general color terms of ordinary dictionary significance are obvious:

Type: Hardy; dwarf; seedling; for cut flowers and for garden decoration.

Class: Miniature.

Breeding: Seedling.

*Seed parent.*—"Perla de Montserrat."

*Pollen parent.*—"Perla de Alcanada."

Propagation: Holds its distinguishing characteristics through succeeding propagations by budding and own root cuttings.

*Flower*

Locality where grown and observed: West Grove, Pennsylvania, U. S. A.

Flowers Borne: Several to stem; in irregular clusters; on stems of medium length and normal strength.

Quantity of bloom: Abundant, in greenhouse.

Continuity: Continuous.

Fragrance: None.

Bud:

*Peduncle.*—Medium length; slender; stiff; medium rough; with medium number of brown hairs. Color—Red overlying Green.

*Before calyx breaks.*—Size—small. Form—ovoid; with a conspicuous neck; with foliaceous appendages on the surface of the bud; with slender, entire foliaceous parts extending beyond the tip of the bud equal to ¾ or more of its length.

*As calyx breaks.*—Color—Spinel Red, Plate 0023.

*As first petal opens.*—Size—small. Form—short; flat; usually singly cuspidate. Color: outside—Indian Lake, Plate 826/3, with basal quarter of petal Pea Green, Plate 61/2; inside—Indian Lake, Plate 826/3, with basal quarter of petal Pod Green, Plate 061/1.

*Opening.*—Opens up well.

Bloom:

*Size (when fully open).*—Medium; from 1¼ to 1½ inches.

*Petalage.*—Very double; from 60 to 73 petals; arranged regularly.

*Form.*—Full at first, but becoming open; petals being flat at first, but becoming loosely rolled outward later at maturity.

Petals:

*Texture.*—Medium leathery.

*Appearance.*—Inside—velvety. Outside—satiny.

*Shape.*—Outer petals—obovate, with base cuspidate. Intermediate petals—obovate, with apex cuspidate. Inner petals—lanceolate.

This description of a newly opened flower was made from a rose grown in a greenhouse in the month of April at West Grove, Pennsylvania, U. S. A.:

*Color.*—Outer petal: outside surface—Tyrian Purple, Plate 727, lighted here and there with Spirea Red, Plate 025, with base of petal Veronese Green, Plate 660/3; inside surface—Rose Bengal, Plate 25, usually with a border of Solferino Purple, Plate 26 at apex of petal, and with base of petal Veronese Green, Plate 660/3. Intermediate petal: outside surface—Tyrian Purple, Plate 727, overcast with Spirea Red, Plate 025, with base of petal Veronese Green, Plate 660/3; inside surface—Tyrian Purple, Plate 727, over main body of petal, with apex of petal Tyrian Purple, Plate 727/1, and with base of petal Veronese Green, Plate 660/3. Inner petal: outside surface—Tyrian Purple, Plate 727, with base of petal White; inside surface—Irridescent Tyrian Purple, Plate 727, with base of petal Veronese Green, Plate 660/3.

This description was made from a rose that was open for three days in a greenhouse in the month of April at West Grove, Pennsylvania, U. S. A.:

*Color.*—Outer petal: outside surface—Rose Bengal, Plate 25, with base of petal Veronese Green, Plate 660/3; inside surface—Solferino Purple, Plate 26, at outer margin, shading to Tyrian Purple, Plate 727/1, and then to a narrow band of Rose Bengal, Plate 25/2, with base of petal Veronese Green, Plate 660/3. Inner petal: outside surface—Rose Bengal, Plate 25, with base of petal Veronese Green, Plate 660/3; inside surface—Tyrian Purple, Plate 727/1, with basal quarter Veronese Green, Plate 660/3.

*General color effect.*—Newly opened flower—Tyrian Purple, Plate 727, with outer margins of outer petals Solferino Purple, Plate 26/1. Three days open—Tyrian Purple, Plate 727/1 over main body of bloom, but with outer margins of outer petals showing Solferino Purple, Plate 26/1.

*Behaviour.*—Drop off cleanly.

*Flower longevity.*—On bush in greenhouse—5 days in April. Cut roses grown in greenhouse and kept at livingroom temperatures—4 days in April.

*Reproductive organs*

Stamens: Very few; arranged irregularly about pistils; mixed with petaloids.
Filaments: Few; some without anthers; short. Color—White.
Anthers: Medium size; all open at once; occasionally an anther fused with a petaloid. Color—Yellow.
Pollen: Sparse. Color—Lemon Yellow, Plate 4.
Pistils: Medium number.
Styles: Uneven; medium length; medium caliper; bunched.
Stigma: Color—Yellow.
Ovaries: All enclosed in receptacle.
Hips: None.
Sepals: Permanent; long; spear-shaped.
Seeds: None.

*Plant*

Foliage:

*Leaves.*—Compound of 3, 5 or 7 leaflets; normal abundance; medium size; moderately thin; leathery.

*Leaflets.* — Shape — lanceolate. Apex — acute. Base—obtuse or acute. Margin—simply serrate.

*Color.*—Mature: upper surface—Spinach Green, Plate 0960; under surface—Spinach Green, Plate 0960/3. Young: upper surface — variable, but generally Spinach Green, Plate 0960/2, often edged with Cardinal Red, Plate 822; under surface—Pod Green, Plate 061, lightly overlaid with Cardinal Red, Plate 822/3.

*Rachis (the supporting stem of the compound leaf).* — Light. Upper side — grooved; hairy. Under side—sparsely thorny.

*Stipules.*—Short; very narrow; with short points turning out at an angle of 45°.

*Disease resistance.*—Average resistance to mildew and black spot, as determined by comparison with other varieties grown under the same cultural conditions at West Grove, Pennsylvania, U. S. A.

Growth:

*Habit.*—Dwarf; upright; much-branched.

*Growth.*—Free.

*Canes.*—Medium caliper.

*Main stems.*—Color—Lettuce Green, Plate 861. Thorns—several; medium length; some straight and some hooked slightly downward; with medium, oval base. Prickles—none. Hairs—none.

*Branches.*—Color—Lettuce Green, Plate 861, overlaid with Brown general coloration. Thorns—several; medium length; straight; with medium, oval base. Prickles—none. Hairs—none.

*New shoots.*—Color—Pod Green, Plate 061, overlaid with Brown general coloration. Thorns—several; medium length; hooked or pointed slightly downward; with medium, oval base. Prickles—none. Hairs—none.

I claim:

A new and distinct variety of rose plant of the miniature class, substantially as herein shown and described, characterized particularly as to novelty by its small, compact, yet vigorous habit of growth, its clean, attractive foliage of appropriate size, its outstandingly good floriferousness, its very double blooms of very good form, and the Tyrian Purple general color tonality of its blooms.

No references cited.